United States Patent [19]

Danby et al.

[11] Patent Number: 4,554,837
[45] Date of Patent: Nov. 26, 1985

[54] REFLECTIVE OPTICAL FLUID PRESSURE SENSOR

[75] Inventors: Hal C. Danby, Palo Alto; Carl Ritson, San Jose, both of Calif.

[73] Assignee: Anatros Corporation, San Jose, Calif.

[21] Appl. No.: 607,060

[22] Filed: May 4, 1984

[51] Int. Cl.[4] ............................................... G01L 7/00
[52] U.S. Cl. ................................... 73/705; 250/231 P
[58] Field of Search ................ 73/705, 747, 749, 293; 250/231 P, 231 R

[56] References Cited

U.S. PATENT DOCUMENTS 1,811,946  6/1931  Bailly ...................................... 73/293
2,841,011  7/1958  Mayes et al. ........................... 73/749

Primary Examiner—Donald O. Woodiel
Attorney, Agent, or Firm—William B. Walker

[57] ABSTRACT

The reflective optical pressure sensor of this invention is a system for measuring the pressure of a liquid comprising a light source and a capillary formed in a transparent solid having a reflective surface positioned in the light path of light from the light source. A light detector is positioned in the path of light originating from the light source which has been reflected by the reflective surface of the capillary. The inlet end of the capillary is open for communication with liquid to be monitored for pressure, and the other end of the capillary is closed or communicates with a closed reservoir. If the pressure of the liquid to be monitored increases, increasing amounts of the liquid pass into the capillary passageway, blocking or reducing light flow to the light detector.

11 Claims, 6 Drawing Figures

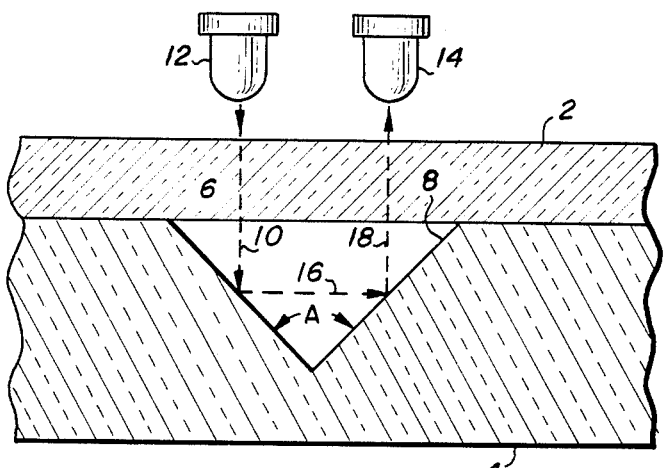
Fig_1
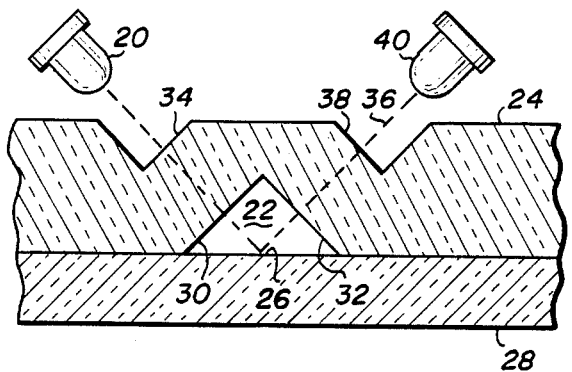
Fig_2
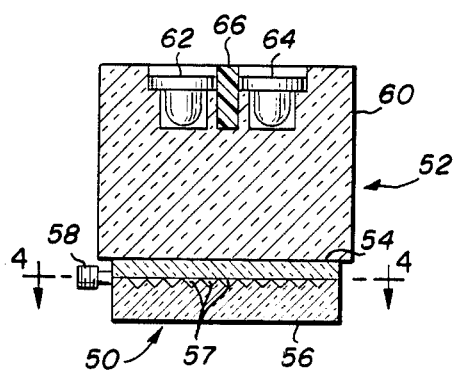
Fig_3
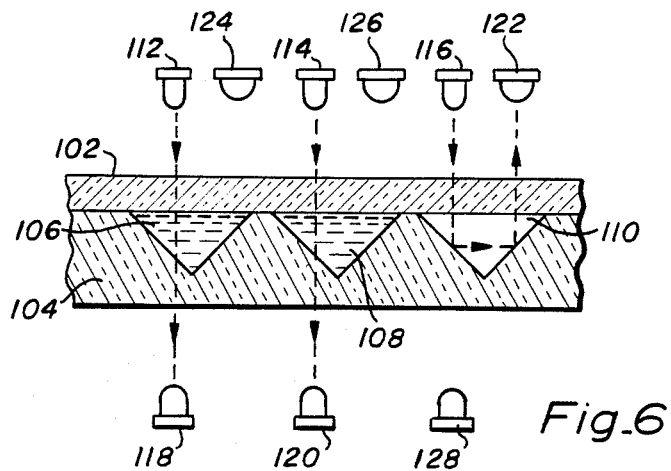
Fig_6

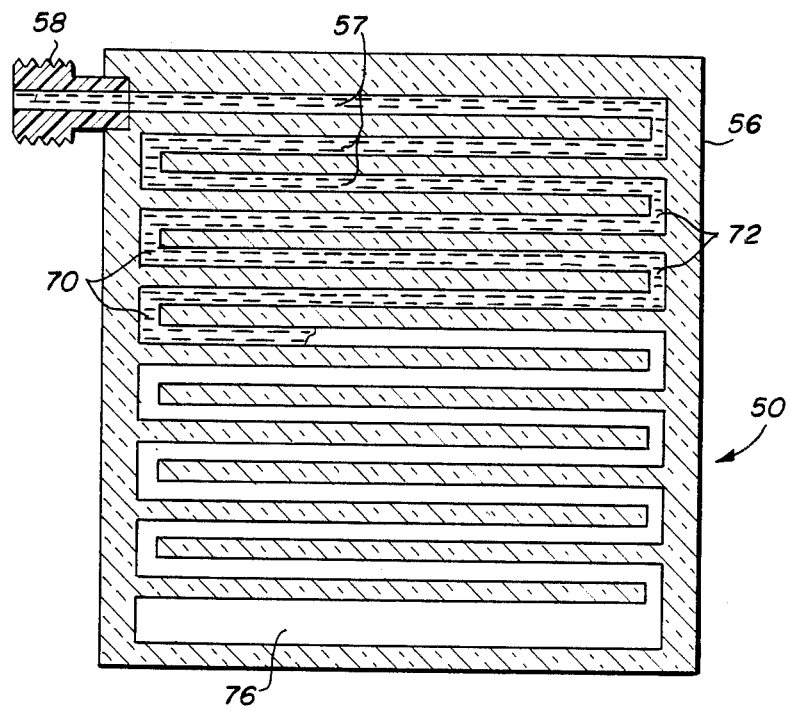
Fig_4
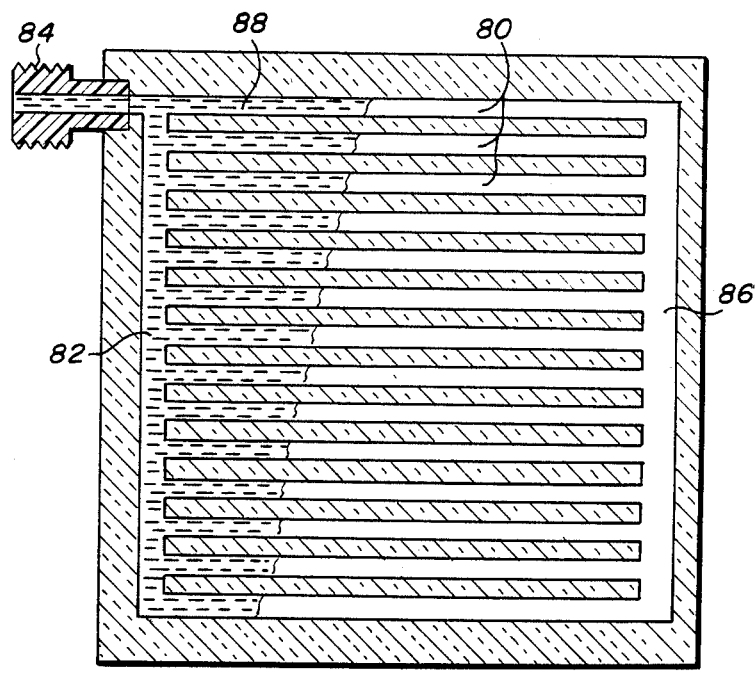
Fig_5

REFLECTIVE OPTICAL FLUID PRESSURE SENSOR

FIELD OF THE INVENTION

This invention relates to the measurement of fluid pressures. In particular, this invention relates to an apparatus for continuously measuring fluid pressure using an reflective optical sensing system.

BACKGROUND OF THE INVENTION

Parenteral solution delivery is usually accomplished using fluid pressure provided by hanging the solution source above the patient. This practice has continued despite the development of newer fluid reservoir systems such as plastic bags and the development of precision pumping systems. Obstructions of the delivery system within the body of the patient are common due to clotting, body movement, infiltration (extravasation), catheter position (proximity of vessel wall to catheter end), vein collapse and the like. This increases fluid pressure in the system between the pump and the patient until the pressure frees the blockage or the motor stops, unless the system has a safety system disengaging the pump motor from the pump or a safety valve releasing the pressure.

Sudden blow-out of the blockage poses a serious danger to the patient. To prevent this, it is necessary to sense any significant increase in fluid pressure between the pump and patient and to immediately stop the pumping action. The devices heretofore available do not have the required sensitivity, and the risk of patient injury from parenteral pump delivery systems continues.

DESCRIPTION OF THE PRIOR ART

Prior to this invention, limited methods have been available to measure fluid pressures. Manometer systems (U.S. Pat. No. 2,817,237) have been used in measuring pressure differentials across flow restrictors to determine fluid flow rates. Bellows with radiation sources (U.S. Pat. No. 3,977,391) have been used. An optical device for measuring pressure differences by means of a light intensity change is described in U.S. Pat. No. 4,322,978. In this system, pressure changes deflect a reflective surface, causing displacement of the light path of reflected light and consequential change in light intensity on a light detector. The device is not suitable for use with parenteral systems.

U.S. Pat. No. 4,398,542 discloses a fluid pressure monitoring system with a pressure diaphram operating on a pressure transducer. Increasing fluid pressure causes movement of the diaphram and increases pressure on the pressure transducer. Piston systems responding to increased fluid pressure to apply increased pressure on pressure transducers are also known. These systems lack the precision and sensitivity required for patient safety.

SUMMARY OF THE INVENTION

The reflective optical pressure sensor of this invention is a system for measuring the pressure of a liquid comprising a light source, a light detector and a capillary. The capillary is a passageway formed in a transparent solid. A reflective surface of the capillary is positioned in the light path of light from the light source. A light detector is positioned in the path of light originating from the light source which has been reflected by the reflective surface of the capillary. The inlet end of the capillary is open for communication with liquid to be monitored for pressure, and the other end of the capillary is closed or communicates with a closed reservoir. If the pressure of the liquid to be monitored increases, increasing amounts of the liquid pass into the capillary passageway and into the capillary area in the path of light from the light source. This reduces light flow to the light detector in direct proportion to the proportion of the capillary area occupied by the liquid, causing a corresponding decrease in electric signal from the light detector. If the liquid entering the capillary passageway is transparent, the proportion of the light reflected by the reflecting surface is greatly reduced and far less light reaches the light detector. If the liquid is not transparent, the light is absorbed, and the amount of reflected light reaching the light detector is reduced to zero. Only very slight increases in liquid pressure cause substantial changes in highly reflective capillary area, providing significant, quantitative changes in light detector output. These can be easily correlated with actual pressure values or used to effect control and safety functions of parental delivery pump systems.

BRIEF DESCRIPTION OF THE DRAWINGS

FIG. 1 is a cross-sectional schematic view of the optical pressure sensor device of this invention having two reflective surfaces.

FIG. 2 is a cross-sectional schematic view of an alternate embodiment of the optical pressure sensor of this invention having a single reflective surface.

FIG. 3 is a cross-sectional view of an embodiment of the reflective optical pressure sensor of this invention.

FIG. 4 is a cross-sectional view of the pressure sensor device of this invention taken along the line 4—4 in FIG. 3 showing a serially connected capillary configuration.

FIG. 4 is a cross-sectional view of the pressure sensor device of this invention showing a parallel connected capillary configuration.

FIG. 6 is a fragmentary cross-sectional view of an alternate embodiment of the reflective optical pressure sensor of this invention.

DETAILED DESCRIPTION OF THE INVENTION

FIG. 1 is a schematic cross-sectional view of an embodiment of the reflective optical pressure sensor of this invention with two reflecting surfaces. The device has a transparent upper plate 2 and a transparent lower plate 4 which have opposing surfaces held together in sealing engagement. These two plates can be bonded together into an integral construction, if desired. The lower plate is optimally selected of material having a desired refractive index, $n_1$, which is near the refractive index of the liquid which will enter the capillary passageway when the liquid pressure increases.

The first reflective surface 6 is positioned in the light path 10 of light from the light source 12 and at an angle with respect to the light path 10 which will direct the light along the desired path to the light detector 14. In the embodiment of FIG. 1, two reflective surfaces 6 and 8 are provided forming an Angle A which is 45 degrees and having the triangular cross-section of an isosceles right triangle. In a plane perpendicular to surfaces 6 and 8, light from the light source 12 traveling along light path 10 will be reflected by surface 6 at a right angle along a path 16, and this will in turn be reflected at a right angle by surface 8 to a new path 18 aligned with the light detector 14. When the open area between the reflective surfaces is filled with air, for example, the amount of light reflected is very high if the surfaces 6 and 8 are smooth and highly reflective. If the open area is filled with a transparent liquid which has a refractive index near the refractive index of the solid material of which plate 4 is composed, most of the light continues through surface 6 into the plate 4 and far less of the light is reflected by the surface 6. This phenomina is repeated at the second reflecting surface 8, even further reducing the amount of light which is reflected back to the detector 14 along path 18. If the open area is filled with a light absorbing liquid such as an opaque liquid, the light from light source 12 is absorbed, and the light from source 12 which reaches detector 14 is reduced to zero.

The light emitting source 12 can be any conventional lamp or light emitting diode. Because the system can be entirely closed to light, the light frequency emitted by the lamp is not critical. Light which is minimally absorbed by the transparent solid material of plates 2 and 4 and which is maximally absorbed by the liquid to be monitored is preferred. Infra-red light is particularly suitable for most transparent solids and most liquids. The light detector 14 is selected to be a light detecting diode which is sensitive to the frequency spectrum of light emitted by the emitter 12.

FIG. 2 is a schematic cross-sectional representation of an alternate embodiment of the optical pressure sensor of this invention with a single reflective surface. In this embodiment, light from light source 20 passes along path 22 through plate 24 until it reaches reflective surface 26 on lower plate 28. Surfaces 30 and 32 form a capillary passageway in the upper plate 24, and the opposed surfaces of plates 24 and 28 are in sealing engagement or integrally joined. The light path 22 is preferably normal to the upper surface 34 of the upper plate 24 in order to minimize refraction and reflective losses. The light path 22 is in a plane perpendicular to the reflective surface 26, and the reflected light proceeds along path 36 through surface 32 and surface 38 to the light detector 40 with which it is aligned. This embodiment operates by the same principles described above with respect to FIG. 1. When transparent liquid enters the open area defined by the surfaces 26, 30 and 32, the amount of light from the light source 20 which is reflected by surface 26 is greatly reduced, reducing the signal from the light detector 40. An opaque or light absorbing liquid totally absorbs the light, permitting no light to reach the light detector.

The embodiment of FIG. 2, in having only one reflecting surface, does not achieve the doubling effect obtained with the dual reflecting surface configuration of the device of FIG. 1. However, it has the advantage that the surfaces 30 and 32 can have any shape desired including an irregular or curved shape without greatly disturbing the function of the device. The special normal surfaces 34 and 38 can also be at any angle or be eliminated if desired, but the efficiency of the device will be correspondingly reduced by reflection and refraction losses.

FIG. 3 is a cross-sectional view of an embodiment of the reflective optical pressure sensor of this invention. The pressure sensor has two components, the capillary plate portion 50 and the light source and detector element 52. The capillary plate portion 50 comprises an upper plate 54 and a lower plate 56 sealingly engaged. The lower plate 56 has capillary passageways 57 corresponding to the shape described above with respect to FIG. 1. The inlet connector 58 communicates with the capillary passageways 57 and is designed to be connected to the liquid source to be monitored.

The element 52 can be a solid plate of transparent material 60, the lower surface thereof contacting the upper surface of the upper plate 54. It has recesses for mounting the light source 62 and the light detector 64. An opaque barrier 66 is provided between the light source 62 and the light detector 64 to prevent direct passage of light therebetween.

FIG. 4 is a cross-sectional view of the pressure sensor device of this invention taken along the line 4—4 in FIG. 3 showing a serially connected capillary configuration. In this view of the pressure sensor capillary plate 50, the lower plate 56 has a plurality of linear passageways 57, the ends thereof being serially connected in a zig-zag configuration by serial connecting passageways 70 and 72. The inlet end of the passageway system communicates with the inlet opening connector 58. The other end of the passageway system communicates with the closed gas reservoir 76.

In operation with the connector 58 communicating with a liquid flow to be monitored for pressure increase, liquid passes into the capillary passageway 57 until the pressure of the gas in the remainder of the capillary system and the reservoir 76 rises sufficiently to balance the liquid pressure and stop the liquid advance. If the liquid pressure increases, liquid again advances into further portions of the capillary system until the gas pressure in the remainder of the system rises to balance the liquid pressure. If the liquid pressure decreases, the gas displaces the liquid from the passageway until the gas and liquid pressures are balanced. As described above with respect to FIG. 1, the portions of the capillary passageways occupied by liquid reflect less of the light from the light source 62, and the amount of light reaching the light detector 64 is correspondingly reduced.

The capillary passageways in this system should be sufficiently small to prevent liquid from bypassing gas in the passageway, entrapping bubbles of gas in the liquid phase. The term "capillary" as used herein is defined to include all dimensions of passageways which meet the above specifications and is not limited to dimensions which provide capillary action. The preferred cross-sectional areas are less than 5 $mm^2$ and are preferably within the range of from 0.1 to 1.0 $mm^2$ for most aqueous solutions.

FIG. 5 is a cross-sectional view of the pressure sensor of this invention showing a parallel connected capillary configuration. In this system, the capillary passageways 80 are arranged in parallel configuration, the inlet openings of each communicating with an inlet manifold or channel 82 which communicates with the inlet connector 84. The outlet openings of the passageways 80 communicate with the closed gas reservoir 86. Liquid 88 which has passed into the capillary area reduces the amount of light reflected by the reflective surfaces of the capillary passageways 80 as described above with respect to FIG. 1. Liquid enters the passageways 80 until the gas pressure in the remainder of the passageways and reservoir 86 balances the liquid pressure in the same manner described above with respect to FIGS. 3 and 4.

The length of the capillary passageways and respective volume ratios of the passageways and the gas reservoir determine the sensitivity of the system. The capillary configuration in FIG. 4 provides greater sensitivity than the configuration in FIG. 5. Higher reservoir to capillary volume ratios also increase sensitivity, requiring the entrance of proportionally more liquid into the passageways before a liquid pressure increase is balanced.

Capillary passageways having a linear, parallel configuration shown in the illustrated embodiments of this invention are merely representative of the shapes of the passageways, and this invention is not limited thereto. The capillary passageways can be a continuous spiral, for example, or be concentric circular paths, connected either in series or in parallel, as desired, with the reservoir in the center or, alternatively, for example, in the outer perimeter.

FIG. 6 is a fragmentary cross-sectional view of an alternate embodiment of the reflective optical pressure sensor of this invention. In this embodiment light detectors are positioned both on the surface of the device facing or opposing the light source and facing the reverse or opposite surface of the device. This embodiment can function both as a reflective optical pressure sensor and as a transmissive optical pressure sensor. The transparent upper plate 102 and transparent lower plate 104 have opposing surfaces held together in sealing engagement. The configuration of the reflective surfaces and refractive index of the material of construction are as described above with respect to FIG. 1.

A plurality of capillary passageways are provided, and for purposes of explanation, passageways 106 and 108 are filled with liquid and passageway 110 is filled with air. Light from light emitting diodes 112, 114 and 116 pass through the upper plate 102. If a transparent liquid is present in the passageways as in passageways 106 and 108, the light passes through the lower plate 104 and can be detected by the light detectors 118 and 120 in the light path thereof.

Light from light source 116 passing through capillary 110, however, is reflected, and impinges on the light detector 122 positioned in the path of the reflected light. In this event, little light would impinge on the light detectors 124, 126 and 128. A greater sensitivity would be achieved with this configuration when comparing the output of the reflective light sensors 122, 124, and 126 and the output of the transmitted light sensors 118, 120, and 128.

If the liquid in the capillaries 106 and 108 were opaque, no light would be transmitted or reflected by them, and the system would function in the same manner as the embodiment of FIG. 1. The light absorbed by the opaque liquid in the capillaries 106 and 108 would not be reflected or transmitted, and neither the detectors 124 and 126 nor the detectors 118 and 120 would receive any light originating from the light emitters 112, 114 and 116. The light detector 122 would receive reflected light originating from light emitter 122, however, since the reflective surfaces in the capillary 110 would be exposed.

The invention claimed is:

1. An optical fluid pressure sensor comprising a light source, a capillary passageway containing a gas and formed in a transparent solid, the capillary passageway having a reflective surface positioned in the light path of light from the light source, and a light detector positioned in the path of light reflected by the reflective surface, the capillary passageway having an inlet end means for receiving liquid from an external source under fluid pressure to be monitored and an outlet end, the outlet end thereof having a closure means for preventing escape of gas therefrom.

2. The optical pressure sensor of claim 1 wherein the light source is a light emitting diode and the light detector is a light detecting diode.

3. The optical pressure sensor of claim 1 wherein capillary passageways are formed in the surface of a first transparent plate against which a second transparent plate is positioned in sealing engagement.

4. The optical pressure sensor of claim 1 wherein the capillary passageway means comprises a plurality of capillary passageways connected in a zig-zag configuration to form a capillary passageway zone.

5. The optical pressure sensor of claim 4 wherein the capillary passageways are linear and parallel, the ends thereof being serially connected.

6. The optical pressure sensor of claim 5 wherein the capillary passageways are formed in the surface of a first transparent plate against which a second transparent plate is positioned in sealing engagement.

7. The optical pressure sensor of claim 4 wherein the capillary passageways are linear and parallel, the inlet ends thereof communicating with and connected by an inlet means and the outlet ends thereof being connected to a closed gas reservoir.

8. The optical pressure sensor of claim 7 wherein the capillary passageways are formed in the surface of a first transparent plate against which a second transparent plate is positioned in sealing engagement.

9. The optical pressure sensor of claim 1 wherein the capillary passageway has first and second reflecting surfaces intersecting at a 45 degree angle, the light path from the light source in a plane perpendicular to the two reflecting surfaces intersecting one of the surfaces at an angle of 45 degrees with the first reflecting surfaces to form a second light path intersecting the second reflecting surface at a 45 degree angle and a third light path from the second reflecting surface, the light detecting means being aligned with the third light path.

10. The optical pressure sensor of claim 9 wherein the light source is a light emitting diode and the light detector is a light detecting diode.

11. The optical pressure sensor of claim 1 wherein light detectors are positioned both in the light path of light from the light source which is reflected by the reflective surface and in the light path of light from the light source which is transmitted through the reflective surface.

* * * * *